United States Patent
Goldfain et al.

(10) Patent No.: US 7,553,020 B2
(45) Date of Patent: Jun. 30, 2009

(54) MEDICAL DIAGNOSTIC INSTRUMENT WITH VARIABLE FOCUS LIQUID LENS

(75) Inventors: Ervin Goldfain, Syracuse, NY (US); Daniel C. Briggs, Menphis, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 271 days.

(21) Appl. No.: 11/541,511

(22) Filed: Sep. 29, 2006

(65) Prior Publication Data
US 2008/0079897 A1  Apr. 3, 2008

(51) Int. Cl.
*A61B 3/14* (2006.01)
*A61B 3/10* (2006.01)
(52) U.S. Cl. .................... 351/206; 351/205; 351/221
(58) Field of Classification Search .......... 351/205, 351/206; 600/109, 162, 163, 167, 200
See application file for complete search history.

(56) References Cited

U.S. PATENT DOCUMENTS

| | | | |
|---|---|---|---|
| 4,146,310 A | | 3/1979 | Kohayakawa et al. |
| 5,300,964 A | * | 4/1994 | Kobayashi ............... 351/207 |
| 6,309,068 B1 | | 10/2001 | Kohayakawa et al. |
| 6,334,682 B1 | | 1/2002 | Takai |
| 6,369,954 B1 | | 4/2002 | Berge et al. |
| 6,390,625 B1 | | 5/2002 | Slawson et al. |
| 6,685,317 B2 | | 2/2004 | Su et al. |
| 6,806,988 B2 | | 10/2004 | Onuki et al. |
| 7,331,670 B2 | * | 2/2008 | Ichikawa ............... 351/206 |
| 7,341,557 B2 | * | 3/2008 | Cline et al. ............ 600/160 |
| 2005/0002113 A1 | | 1/2005 | Berge |
| 2005/0110949 A1 | | 5/2005 | Goldfain et al. |
| 2007/0010710 A1 | * | 1/2007 | Perez ................... 600/118 |
| 2007/0156021 A1 | * | 7/2007 | Morse et al. ........... 600/167 |
| 2008/0030682 A1 | * | 2/2008 | Teige et al. ............ 351/206 |
| 2008/0165320 A1 | * | 7/2008 | Helberger ............. 351/206 |

OTHER PUBLICATIONS

B. Berge and J. Pesaux, "Variable Focal Lens Controlled By An External Voltage: An Application of Electrowetting," Eur. Phys. J. E.3, 159-163 (2000).

* cited by examiner

*Primary Examiner*—Jordan M. Schwartz
(74) *Attorney, Agent, or Firm*—Hiscock & Barclay, LLP; Stephen Rosenholm

(57) ABSTRACT

A diagnostic instrument includes an illumination system for providing illuminating light and an imaging system for directing the illuminating light to a target and for transmitting light reflected from the target to a viewing location. The imaging system includes an electrically controllable variable focus liquid lens assembly for focusing the light reflected from the target at the viewing location. The liquid lens assembly includes at least one liquid lens including a housing filled with a first liquid, and a drop of a second liquid being in contact with the first liquid in a predetermined form. The lens further includes a first electrode insulated from the second liquid and a second electrode in electrical contact with the first liquid. A variable voltage control selectively applies a voltage to the first and second electrodes to vary the focus of the lens. An electronic imager is provided to capture the reflected target image.

17 Claims, 6 Drawing Sheets

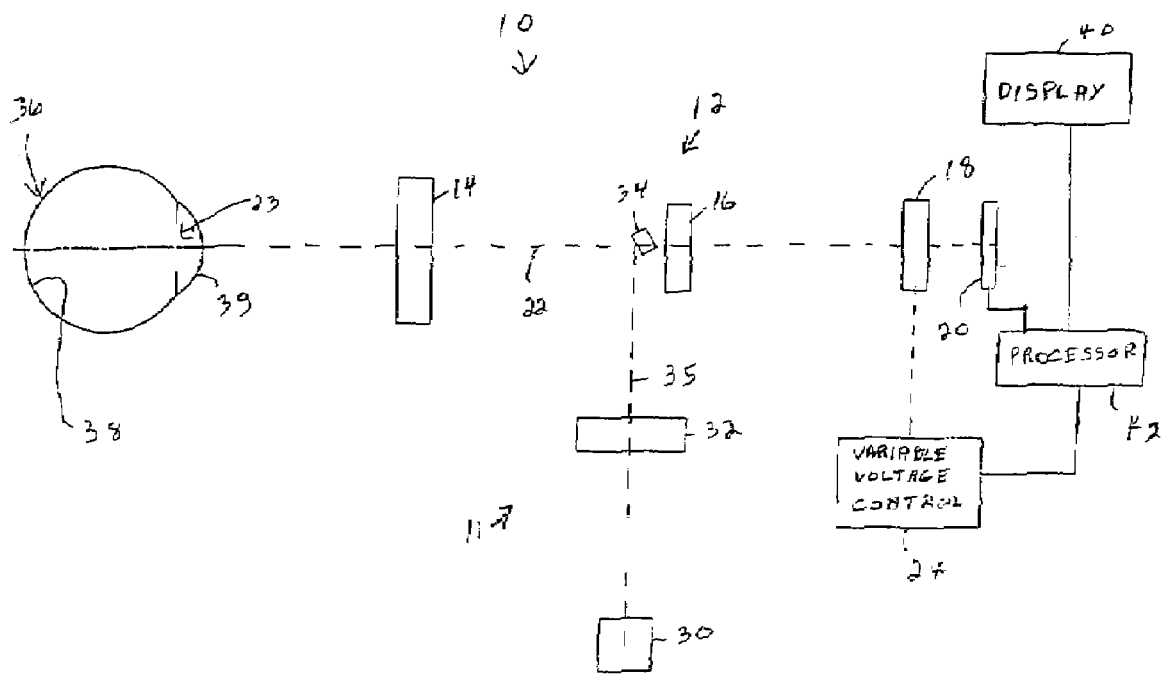
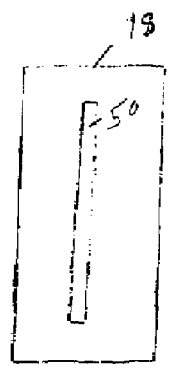
FIG. 2A
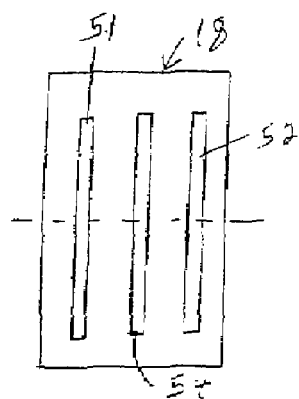
FIG. 2B

MEDICAL DIAGNOSTIC INSTRUMENT WITH VARIABLE FOCUS LIQUID LENS

FIELD OF THE INVENTION

This invention relates in general to medical diagnostic instruments and more specifically to medical diagnostic instruments having a variable focus liquid lens whose focal length is electrically controllable.

BACKGROUND OF THE INVENTION

Medical diagnostic instruments such as ophthalmoscopes, otoscopes, colposcopes and the like, are widely used in the health care field to examine both external regions and externally accessible internal regions of a patient, such as a human or an animal. The instrument typically includes an illuminating system for producing illuminating light, an imaging system for directing the illuminating light on a target, such as the retina of the eye of a patient, and for transmitting light reflected from the target to a viewing region, such as an eyepiece of the instrument viewed by a health care professional. The reflected light image from the target can also be transmitted to an electronic imager, such as a CCD or CMOS imager, which produces an electronic image that can be viewed on a display, that can be further processed, or that can be archived for future reference. (The following are of interest in disclosing eye diagnostic instruments which use electronic imagers: U.S. Pat. No. 4,146,310, issued Mar. 27, 1979, inventors Kohayakawa et al.; U.S. Pat. No. 6,334,682 B1, issued Jan. 1, 2002, inventor Takai; U.S. Pat. No. 6,309,068 B1, issued Oct. 30, 2001, inventor Kohayakawa; U.S. Pat. No. 6,685,317 B2, issued Feb. 3, 2004; and U.S. Patent Application Publication No. 2005/0110949 A1, published May 26, 2005, inventors Goldfain et al.).

Whether viewed live by a health care professional or captured by an electronic imager, the reflected light image of the target must be in focus for the viewer or for the electronic imager, in order to be usable. In known apparatus, focus of a reflected image is obtained by using an optical assembly that has one or more optical elements which can be moved relative to each other. This is desirable in an eyepiece of an ophthalmoscope, for example, in order to adjust the position of the eyepiece focal plane relative to the image of the retina of a patient's eye being viewed to compensate for the refractive error of either the patient or the health care professional. U.S. Pat. No. 6,390,625 B1, issued May 21, 2002, inventors Slawson et al., discloses a manually operable focusing mechanism for an optical instrument. Although suitable for the purposes for which it was intended, it would be desirable to provide a focusing mechanism that is simple, compact, provides the desired dynamic range and which has no moving parts.

A recent development in optics is the variable focus liquid lens disclosed in U.S. Pat. No. 6,369,954 B1, issued Apr. 9, 2002, inventors Berge et al. As disclosed, the variable focus liquid lens comprises a chamber filled with a first liquid, a drop of a second liquid being disposed at least on a region of a first surface of an insulating wall of the chamber, the first and second liquids being immiscible, of different optical indexes, and of substantially same density. The first liquid is conductive and the second liquid is insulating. The lens further comprises means for applying a voltage between the conductive first liquid and an electrode placed on the second surface of the wall; and centering means for maintaining the centering of the edge of the drop while the voltage is applied and for controlling the shape thereof. (See also: U.S. Patent Application Publication No. U.S. 20005/0002113 A1, published Jan. 6, 2005, inventor Berge.) U.S. Pat. No. 6,806,988, issued Oct. 19, 2004, inventors Onuki et al., discloses use of such a variable focus lens in a CCD imager system. The Varioptic Company, Lyon, France, a supplier of variable focus liquid lenses, suggests several medical equipment applications of such a lens on its website. Suggested uses are endoscopy, imaging by confocal microscopy, laser beam focus, control on tumours, and ophthalmology. (See also: the article "Variable focal lens controlled by an external voltage: An application of electrowetting", by B. Berge and J. Pesaux, Eur. Phys. J. E. 3, 159-163 (2000), which suggests (page 163) "[E]ndoscopy could benefit from the compactness of the lens [i.e., variable focus liquid lens] - - - "). However, none of these references disclose specific configurations as to how an electrically controllable variable focus liquid lens can be incorporated into an optical medical diagnostic instrument.

There is thus a need in medical diagnostic instruments of an optical focusing system that is simple, compact, provides the desired dynamic range, has no moving parts, consumes a minimum of electrical power, and can be readily incorporated into existing instrument designs.

SUMMARY OF THE INVENTION

According to the present invention there is provided a solution to these problems and fulfillment of these needs.

According to a feature of the present invention there is provided a medical diagnostic instrument comprising:

an illuminating system for providing illuminating light;

an imaging system for directing said illuminating light to a target and for transmitting light reflected from said target to a viewing location;

wherein said imaging system includes an electrically controllable variable focus liquid lens assembly for focusing said light reflected from said target at said viewing location; and wherein said liquid lens assembly includes at least one liquid lens including a housing filled with a first liquid, and a drop of a second liquid being in contact with said first liquid in a predetermined form, the first and second liquids being immiscible, of different optical indexes, and of substantially same density; wherein the first liquid is conductive and the second liquid is insulating; and wherein the lens further includes a first electrode insulated from said second liquid and a second electrode in electrical contact with said first liquid; and a variable voltage control for selectively applying a voltage to said first and second electrodes to vary the focal length of said lens.

According to another feature of the present invention there is provided a medical diagnostic instrument comprising:

an illuminating system for providing illuminating light;

an electronic imager;

an imaging system for directing said illuminating light to a target and for transmitting light reflected from said target to said electronic imager;

wherein said imaging system includes an electrically controllable variable focus liquid lens assembly for focusing said light reflected from said target onto said electronic imager; and wherein said liquid lens assembly includes at least one liquid lens including a housing filled with a first liquid, and a drop of a second liquid being in contact with said first liquid in a predetermined form, the first and second liquids being immiscible, of different optical indexes, and of substantially same density; wherein the first liquid is conductive and the second liquid is insulating; and wherein the lens further includes a first electrode insulated from said second liquid and a second electrode in electrical contact with said first liquid; and a variable voltage control for selectively applying a voltage to said first and second electrodes of said at least one liquid lens to vary the focal length of said lens.

According to still another feature of the present invention there is provided a medical diagnostic instrument comprising:

an illumination system for providing illuminating light;
an electronic imager;
an imaging system for directing said illuminating light to a target and for transmitting light reflected from said target to said electronic imager;
wherein said imaging system includes an electrically controllable variable focus liquid lens assembly for focusing said light reflected from said target onto said electronic imager; and wherein said liquid lens assembly includes first and second spaced liquid lenses, and wherein each of said first and second liquid lenses includes a housing filled with a first liquid, and a drop of a second liquid being in contact with said first liquid in a predetermined form, the first and second liquids being immiscible, of different optical indexes, and of substantially same density; wherein the first liquid is conductive and the second liquid is insulating; and wherein the lens further includes a first electrode insulated from said second liquid and a second electrode in electrical contact with said first liquid; and a variable voltage control for selectively applying a voltage to said first and second electrodes of each of said first and second liquid lenses to vary the focal length of each of said lens.

The present invention incorporates an optical focusing system that is simple, compact, provides the desired dynamic range, has no moving parts, consumes a minimum of electrical power, and can be readily incorporated into existing instrument designs.

These and other features and advantages of the present invention will become clear to those skilled in the art from a careful reading of the detailed description of the invention in connection with the referenced drawings.

BRIEF DESCRIPTION OF THE DRAWINGS

The preferred embodiment(s) of the invention will now be described by way of example only, with reference to the accompanying figures wherein like elements bear like reference numerals.

FIG. 1 is a diagrammatic view of an embodiment of the present invention as used in an ophthalmoscope.

FIGS. 2A and 2B are more detailed diagrammatic views of the variable focus lens of FIG. 1.

DETAILED DESCRIPTION OF THE INVENTION

Figure 3:
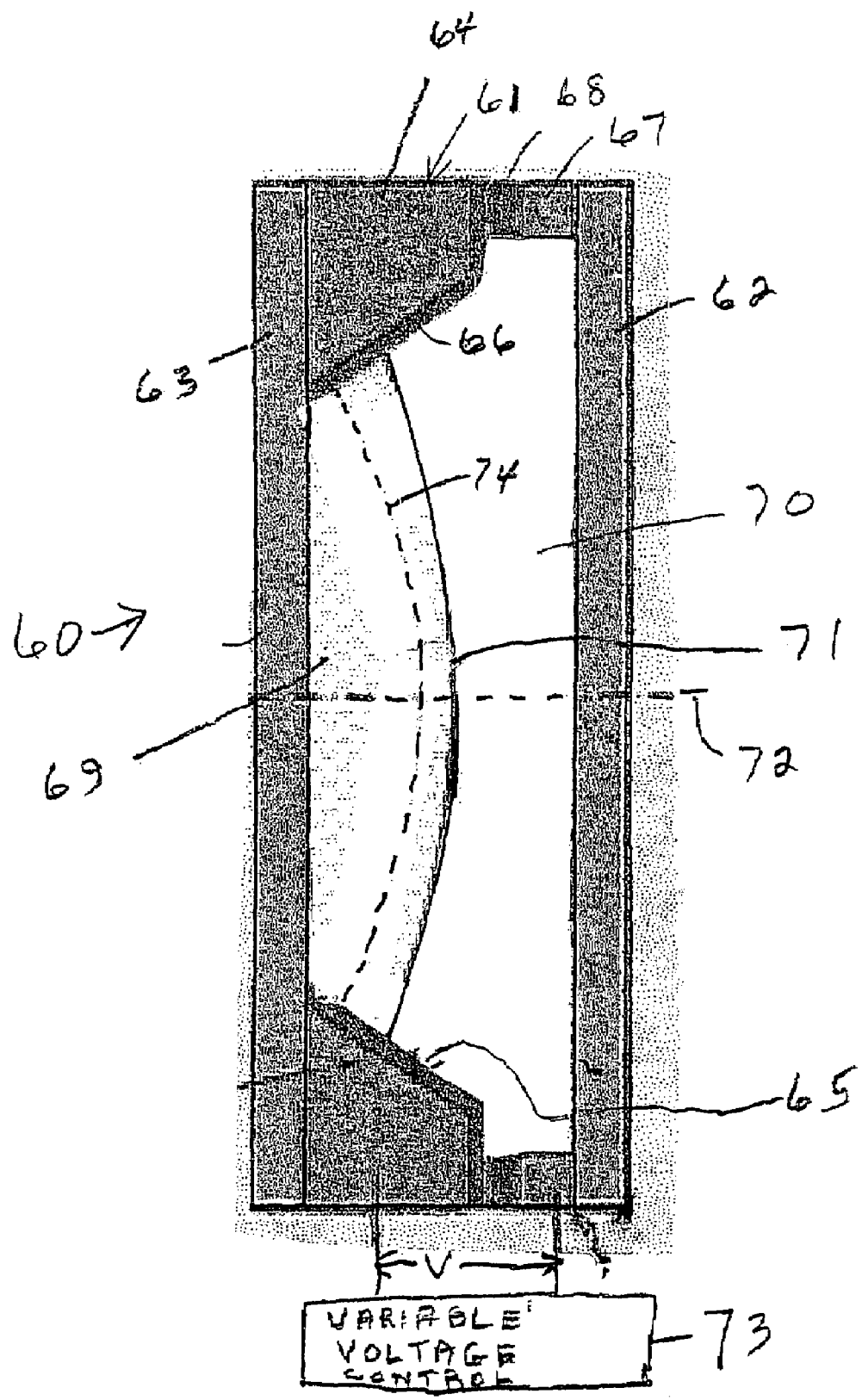
FIG. 3 is a diagrammatic view of an electrically controllable variable focus liquid lens which can be used in the present invention.

In general, the present invention provides a medical diagnostic instrument that utilizes an electrically controllable focusing system that is simple, compact, provides the desired dynamic range, has no moving parts, consumes a minimum of electrical power, and can be incorporated into existing instrument designs. The focusing system includes one or more liquid lenses, whose focal length can be varied through electrical control. The image produced by the instrument is focused for direct viewing and/or for acquisition by an electronic imager which produces a digital image that can be processed, displayed, archived, or the like. Although the example below relates to an ophthalmoscope, the invention is also applicable for use in other medical diagnostic instruments, such as, otoscopes, colposcopes, vaginal specula devices, skin imaging devices, retinoscopes, retinal imagers, slit lamps, autorefractors, corneal topographers, and the like.

Referring now to FIG. 1, there is diagrammatically shown an embodiment of the present invention constituting an ophthalmoscope for use in illuminating and forming an image of a target such as the retina or cornea of a patient's eye. As shown, ophthalmoscope 10 includes an illuminating system 11 and an imaging system 12. Imaging system 12 includes objective lens 14 (which also forms part of the illumination system), imaging lens 16, variable focus liquid lens assembly 18, and electronic imager 20 spaced along imaging axis 22. Lens assembly 18 is controlled by variable voltage control 24. Electronic imager can be any known imager such as a CCD or CMOS imager. During examination of a patient, imaging axis 22 is approximately coincident with the optical axis of a patient's pupil 23. In all references herein, the terms "lens" and "lens assembly" can refer to a single optical element or a plurality of optical elements functioning together.

Illuminating system 11 includes a light source 30, a condensing lens 32 and mirror 34 spaced along illuminating axis 35. Light source 30 can be any generic light source, such as a filament based lamp, a metal halide lamp, a Xenon lamp, the end face of a fiber optic cable, a laser diode, or a single or multiple LED array. Condenser lens 32 converges light from light source 30 onto mirror 34 which reflects the illuminating light along axis 22 to objective lens 14 which transmits light which converges at cornea 39 and diverges inside eye 36 of a patient to illuminate a wide area of retina 38. Light reflected from retina 38 is transmitted along imaging axis 22 by objective lens 14, imaging lens 16, and focusing lens assembly 18 to electronic imager 20. Imager 20 produces an electronic (digital) image which is displayed on display 40 after being processed by processor 42. Processor 42 can be programmed to control imager 20 and to capture and also store image data generated by and received from imager 20. Processor 42 can be operated by autofocus software wherein an image displayed on display 40 is automatically focused through lens control 24 and lens 18. Processor 42 detects the image state of focus and drives the liquid lens to obtain the sharpest image. Processor 42 can be located within instrument 10 or located external to instrument 10. If located externally, processor 42 can communicate with imager 20 either through wired or wireless communication channels.

The components of the instrument are preferably contained in a housing that can be hand held. Alternatively, the components of the instrument can be contained in a fixed housing located on a table or the floor.

According to the present invention, lens assembly 18 includes one or more electrically controllable variable focus liquid lenses. As shown in FIG. 2A, lens assembly 18 includes one variable focus liquid lens 50. As shown in FIG. 2B lens assembly 18 includes first and second spaced variable focus liquid lenses 51 and 52 with a variable iris 54 located between lenses 50 and 52. Iris 54 controls the amount of light passed through lens assembly 18.

FIG. 3 is a diagrammatic view of a preferred variable focus liquid lens. As shown, variable focus liquid lens 60 includes a housing 61 that incorporates a pair of parallel transparent windows 62 and 63, first electrode 64 having a frustro-conical opening 65, insulating layer 66 on first electrode 64, second electrode 67, insulator 68, a drop of insulating liquid 69 located on conical insulating layer 66 and on window 63, and electrically conductive liquid 70 filling the rest of housing 61. Conductive liquid 70 is in electrical contact with second electrode 67. Insulating liquid 69 and conductive liquid 70 are in contact along a meniscus region represented by solid line 71. The insulating liquid 69 and conductive liquid 70 are both transparent, are immiscible, have different optical indexes, and have substantially the same density. Conductive liquid 69 can, for example, be water mixed with salts and insulative liquid 70 can be oil.

When no voltage is applied, the system is said to be at rest. In this configuration the drop of insulating liquid 69 naturally takes the shape of the solid line designated by reference curve 71. An axis 72 is perpendicular to the window 62 and passes through the center of 71. At rest, the drop of insulating liquid 69 is centered about axis 72 which constitutes the optical axis of the lens.

Applying a non-zero voltage V from variable voltage control 73 between first electrode 64 and second electrode 67 creates an electrical field localized in the region surrounding the electrodes. As a consequence, conductive liquid 70 deforms insulating liquid drop 69 and the reference curve 71 takes the shape designated by the dashed line 74. This results in a variation of the focal length of the liquid lens. A range of applied voltages will result in a range of various radii of curvature for the dashed line 74 and a corresponding range of optical powers for the liquid lens.

Referring now to FIGS. 4-7, there are shown further embodiments of the present invention which are modifications of the embodiment shown in FIG. 1. In each Figure, like elements will bear like reference numerals.

Figure 4:
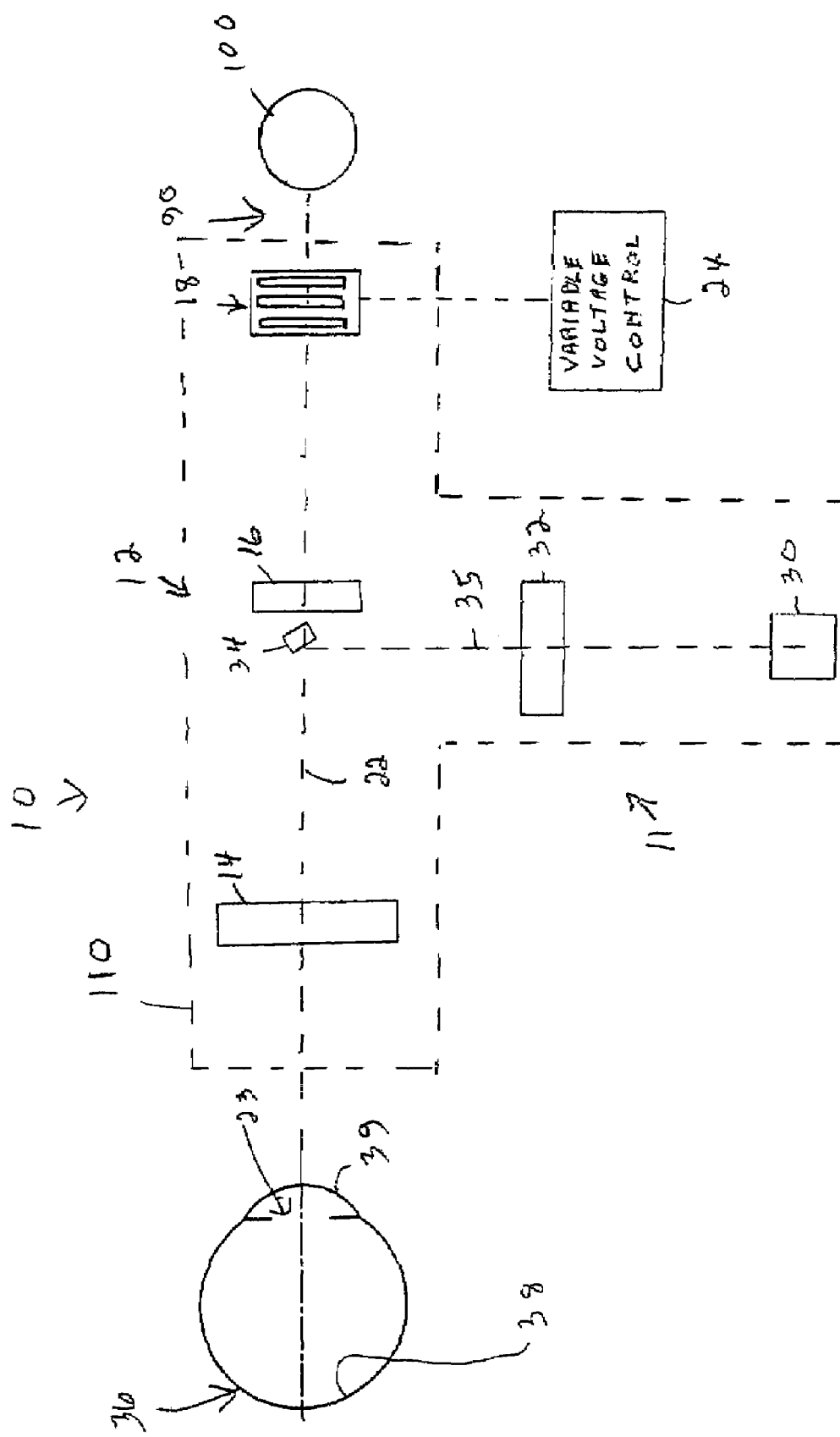
FIGS. 4-7 are diagrammatic views of other embodiments of the present invention.

As shown in FIG. 4, the reflected eye image is transmitted directly to a viewing location 90 to be viewed by health care professional 100. The components of instrument 10 are shown housed in dashed-line hand held housing 110. In this embodiment, the patient's eye will be directly viewed by a health care professional 100.

Figure 5:
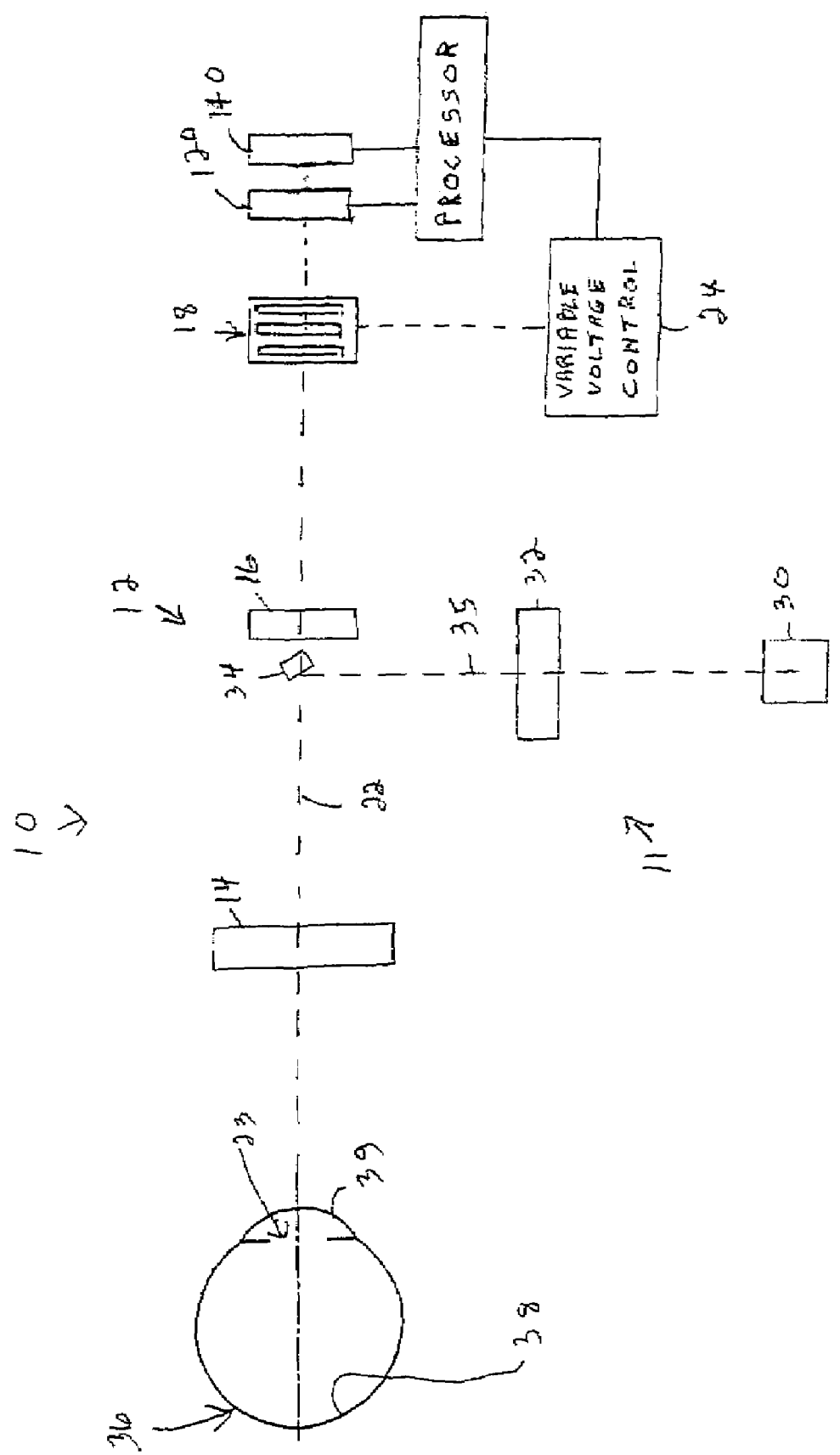

As shown in FIG. 5, the reflected eye image is transmitted to electronic imager 120 which is in alignment with display 140 on axis 22. Imager 120 produces an electronic image which is displayed on display 140 and viewed in real time by a health care professional.

Figure 6:
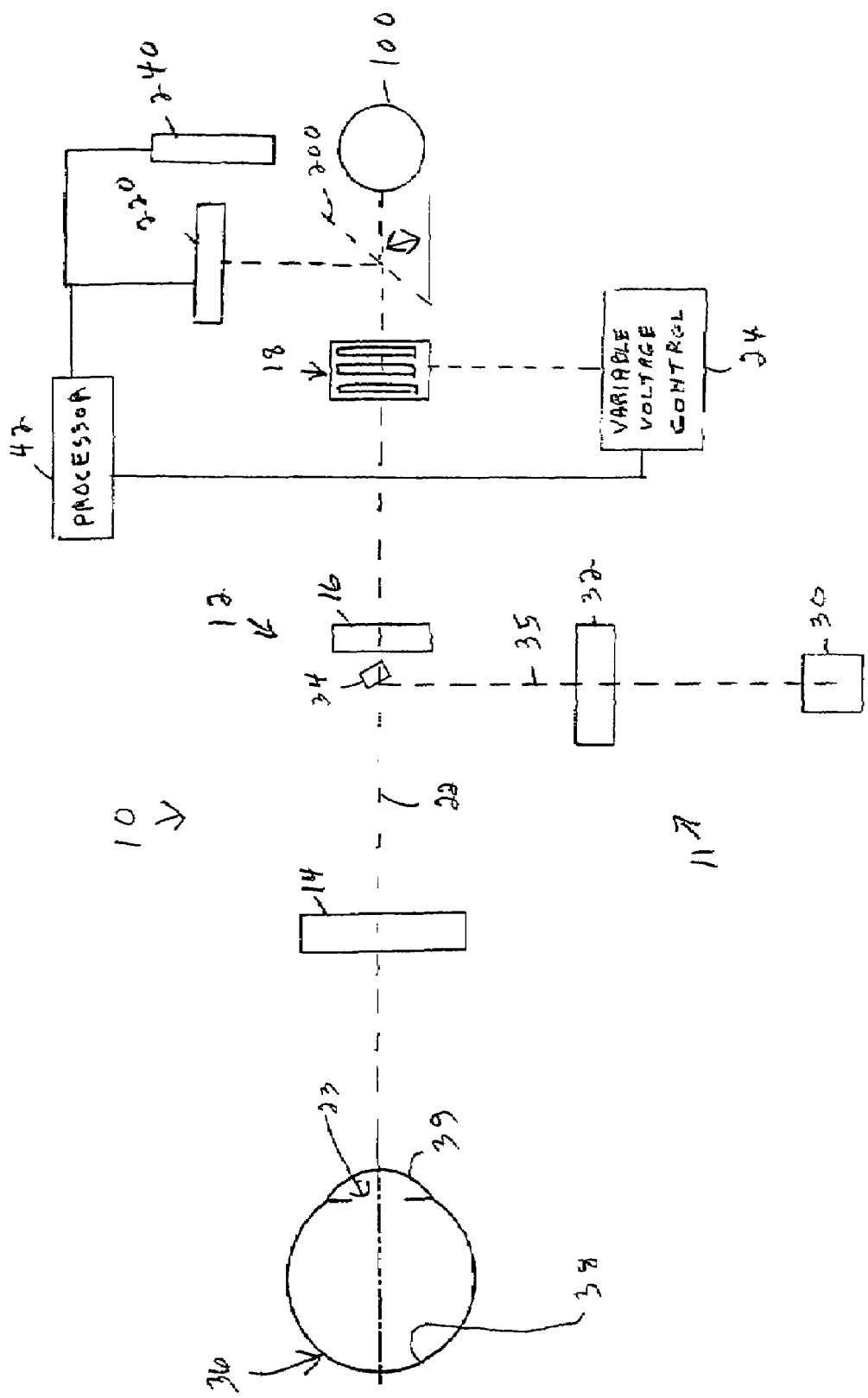

As shown in FIG. 6, a mirror 200 is movably positioned between a first position out of axis 22, as shown as a solid line and a second position intercepting axis 22 at a arbitrary folding angle, as shown as dashed lines. Mirror 200 can be configured to be moved manually or automatically by means of a solenoid, motor or the like. In the first position of mirror 200, the reflected eye image is viewed directly by health care professional 100. In the second position of mirror 200, the reflected eye image is transmitted to imager 220 which produces an image displayed on display 240. In this embodiment, the eye image can be sequentially viewed by the health care professional.

Figure 7:
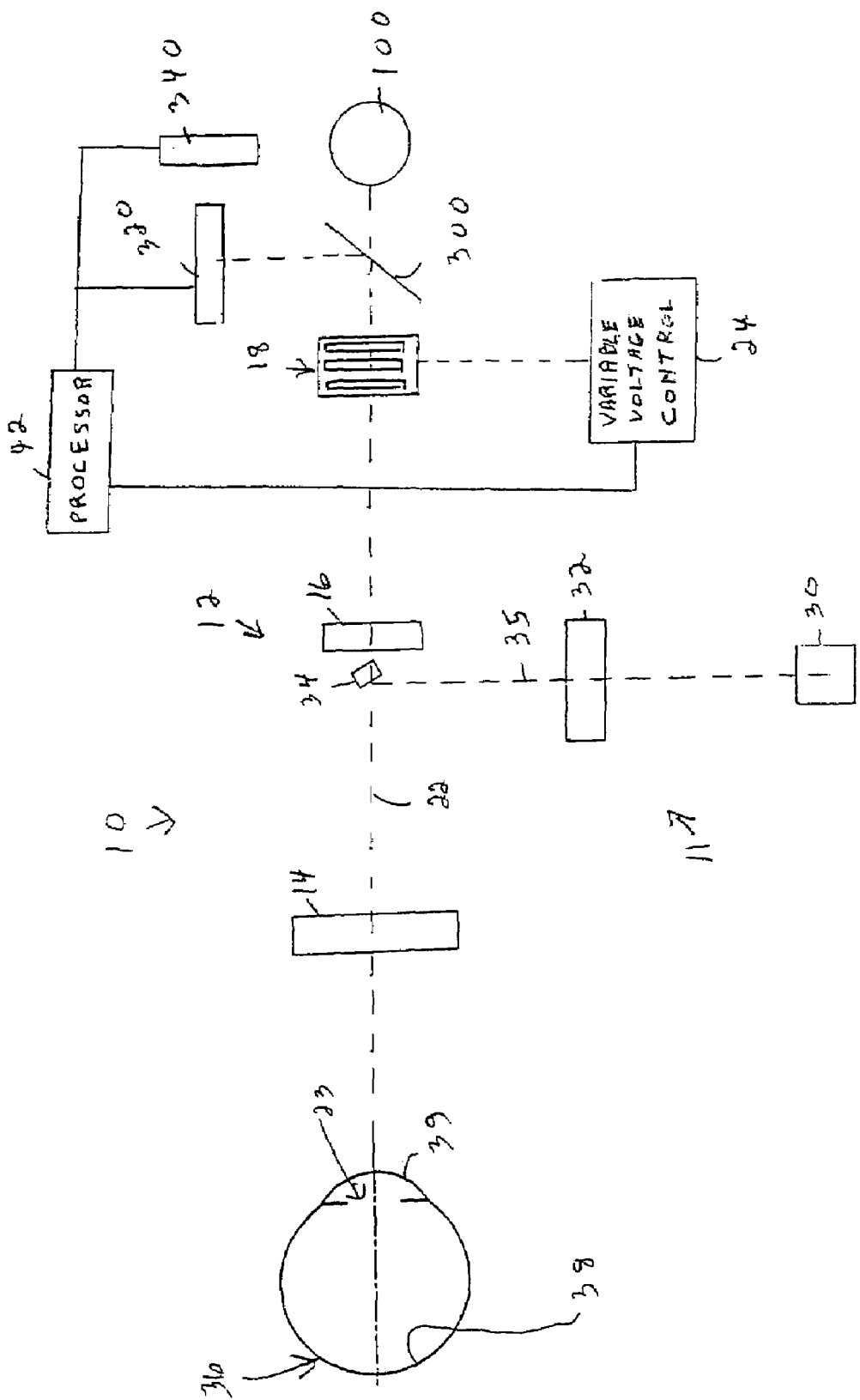

As shown in FIG. 7, a beam splitter 300 intersects axis 22 at an arbitrary folding angle. The eye image is transmitted directly by beam splitter 300 to health care professional 100. Simultaneously, beam splitter 300 reflects the eye image to electronic imager 320 which produces an electronic image which is displayed on display 340. Thus, the reflected eye image can be simultaneously viewed directly and on the electronic display. The image on display 340 can be processed in numerous ways well known to those skilled in the art.

While the present invention has been particularly shown and described with reference to the structure and methods disclosed herein and as illustrated in the drawings, it is not limited to the details set forth and this invention is intended to cover any modifications and changes as may come within the spirit and scope of the following claims.

PARTS LIST

10—ophthalmoscope
11—illuminating system
12—imaging system
14—objective lens
16—imaging lens
18—variable focus liquid lens assembly
20—electronic imager
22—imaging axis
23—patient's pupil
24—variable voltage control
30—light source
32—condenser lens
34—mirror
35—illuminating axis
36—eye
38—retina
39—cornea
40—display
42—processor
50, 51, 52—variable focus liquid lens
54—iris
60—variable focus liquid lens
61—housing
62, 63—window
64—first electrode
65—frustro-conical opening
66—insulating layer
67—second electrode
68—insulator
69—insulating liquid
70—conductive liquid
71—reference curve
72—optical axis
73—variable voltage control
74—reference
100—health care professional
110—hand held housing
120—electronic imager
140—display
200—mirror
220—electronic imager
240—display
300—beam splitter
320—electronic imager
340—display

What is claimed is:

1. A medical diagnostic instrument comprising:
an illuminating system for providing illuminating light;
an imaging system for directing said illuminating light to a target and for transmitting light reflected from said target to a viewing location;
wherein said imaging system includes an electrically controllable variable focus liquid lens assembly for focusing said light reflected from said target at said viewing location; and
wherein said liquid lens assembly includes first and second spaced liquid lenses; and
wherein each of said first and second liquid lenses includes a housing filled with a first liquid, and a drop of a second liquid being in contact with said first liquid in a predetermined form, the first and second liquids being immiscible, of different optical indexes, and of substantially same density;

wherein the first liquid is conductive and the second liquid is insulating; and wherein each of said lenses further include a first electrode insulated from said second liquid and a second electrode in electrical contact with said first liquid; and a variable voltage control for selectively applying a voltage to said first and second electrodes to vary the focal length of each of said lenses; and including a variable iris located between said first and second liquid lenses.

2. The medical diagnostic instrument of claim 1 including a hand held housing for housing said illuminating system and said imaging system, including said liquid lens assembly.

3. The medical diagnostic instrument of claim 1 wherein said illumination system includes a small point-like light source.

4. The medical diagnostic instrument of claim 3 wherein said point-like light source is one of a filament based lamp, an arc lamp, a fiber optic light source, and a solid state light source.

5. A medical diagnostic instrument comprising:

an illuminating system for providing illuminating light;

an electronic imager;

an imaging system for directing said illuminating light to a target and for transmitting light reflected from said target to said electronic imager;

wherein said imaging system includes an electrically controllable variable focus liquid lens assembly for focusing said light reflected from said target onto said electronic imager; and wherein said liquid lens assembly includes first and second spaced liquid lenses, and wherein each of said first and second liquid lenses includes a housing filled with a first liquid, and a drop of a second liquid being in contact with said first liquid in a predetermined form, the first and second liquids being immiscible, of different optical indexes, and of substantially same density; wherein the first liquid is conductive and the second liquid is insulating; and wherein each of said lenses further include a first electrode insulated from said second liquid and a second electrode in electrical contact with said first liquid; and a variable voltage control for selectively applying a voltage to said first and second electrodes of each of said liquid lenses to vary the focal length of said lenses; and including a variable iris located between said first and second liquid lenses: and wherein said illumination system includes a small point-like light source.

6. The medical diagnostic instrument of claim 5 including a hand held housing for housing said illuminating system and said imaging system, including said liquid lens assembly.

7. The medical diagnostic instrument of claim 6 wherein said point-like light source is one of a filament based lamp, an arc lamp, a fiber optic light source, and a solid state light source.

8. A medical diagnostic instrument comprising:

an illumination system for providing illuminating light;

an electronic imager;

an imaging system for directing said illuminating light to a target and for transmitting light reflected from said target to said electronic imager;

wherein said imaging system includes an electrically controllable variable focus liquid lens assembly for focusing said light reflected from said target onto said electronic imager; and wherein said liquid lens assembly includes first and second spaced liquid lenses, and wherein each of said first and second liquid lenses includes a housing filled with a first liquid, and a drop of a second liquid being in contact with said first liquid in a predetermined form, the first and second liquids being immiscible, of different optical indexes, and of substantially same density;

wherein the first liquid is conductive and the second liquid is insulating; and wherein the each of said lenses further include a first electrode insulated from said second liquid and a second electrode in electrical contact with said first liquid; and a variable voltage control for selectively applying a voltage to said first and second electrodes of each of said first and second liquid lenses to vary the focal length of each of said lenses; and including a variable iris located between said first and second liquid lenses.

9. The medical diagnostic instrument of claim 8 wherein said imaging system includes an imaging axis and wherein said electronic imager is located on said imaging axis.

10. The medical diagnostic instrument of claim 9 including a display for displaying an image acquired by said electronic imager, wherein said display is located on said imaging axis and wherein said displayed image is viewable to a user of said instrument.

11. The medical diagnostic instrument of claim 8 wherein said imaging system includes an imaging axis, wherein said electronic imager is spaced from said imaging axis, and wherein said variable focus liquid lens assembly produces a substantially focused image which is directly viewable along said imaging axis and which can be acquired by said electronic imager.

12. The medical diagnostic instrument of claim 11 including a movably mounted mirror located past said liquid lens assembly which is movable between a first position out of the path of said imaging axis and a second position in the path of said imaging axis to reflect a focused image to said electronic imager.

13. The medical diagnostic instrument of claim 11 including a beam splitter located past said liquid lens assembly in the path of said imaging axis for transmitting a focused image along said imaging axis for direct viewing by an instrument user and for simultaneously reflecting the focused image to said electronic imager.

14. The medical diagnostic instrument of claim 8 including a processor for controlling said electronic imager.

15. The medical diagnostic instrument of claim 14 wherein said processor also controls said variable voltage control and wherein said processor includes an automatic focus control feature for automatically controlling said variable voltage control as a function of the image state of focus of an image acquired by said electronic imager.

16. The medical diagnostic instrument of claim 8 including a hand held housing for housing said illuminating system and said imaging system, including said liquid lens assembly.

17. The medical diagnostic instrument of claim 16 wherein said hand held housing also houses said electronic imager.

* * * * *